United States Patent [19]

Thornander

[11] Patent Number: 5,010,887
[45] Date of Patent: Apr. 30, 1991

[54] NOISE DISCRIMINATION IN IMPLANTABLE PACEMAKERS

[75] Inventor: Hans T. Thornander, Paris, France

[73] Assignee: Siemens-Pacesetter, Inc., Sylmar, Calif.

[21] Appl. No.: 438,818

[22] Filed: Nov. 17, 1989

[51] Int. Cl.$^5$ ............................................. A61B 5/04
[52] U.S. Cl. .............................. 128/696; 128/419 PG; 128/901; 128/708
[58] Field of Search .......... 128/696, 419 PG, 419 PT, 128/706, 691, 708, 901

[56] References Cited

U.S. PATENT DOCUMENTS

| | | | |
|---|---|---|---|
| 3,858,034 | 12/1974 | Anderson | 235/151.3 |
| 4,000,461 | 12/1976 | Barber et al. | 324/102 |
| 4,129,133 | 12/1978 | Irnich et al. | 128/419 |
| 4,173,230 | 11/1979 | Digby | 128/419 |
| 4,250,889 | 2/1981 | Levin | 128/708 |
| 4,263,919 | 4/1981 | Levin | 128/901 |
| 4,458,692 | 7/1984 | Simson | 128/705 |
| 4,478,224 | 10/1984 | Bailey | 128/706 |
| 4,686,988 | 8/1987 | Sholder | 128/419 |
| 4,712,555 | 12/1987 | Thornander et al. | 128/419 |
| 4,790,317 | 12/1988 | Davies | 128/419 D |
| 4,830,020 | 5/1989 | Ruth | 128/691 |
| 4,913,146 | 4/1990 | DeCote, Jr. | 128/419 PG |

OTHER PUBLICATIONS

U.S. Patent Application Ser. No. 793,538 (Davies), filed 10/31/85.

*Primary Examiner*—Francis Jaworski
*Assistant Examiner*—Manuel George
*Attorney, Agent, or Firm*—Bryant R. Gold; Malcolm J. Romano

[57] ABSTRACT

A noise discrimination circuit determines if sensed electrocardiographic (ECG) pulsed signals sensed within a pulse generator are valid ECG signals, i.e., valid P-waves or R-waves, or noise. The ECG signal may then be processed. The processed ECG signal is monitored to determine both the amplitude and duration of any signal pulses appearing thereon. If the amplitude of a given ECG signal pulse exceeds a prescribed threshold level for a prescribed time period, the pulse is considered to be a valid ECG signal. The noise discrimination circuit includes: a threshold detector for determining if the amplitude of the ECG signal exceeds the prescribed threshold level; a timer circuit for generating a timed window signal, triggered by the threshold detector whenever the ECG signal amplitude exceeds the prescribed threshold level; and logic circuitry for determining if the amplitude of the ECG signal remains above the threshold level for the duration of the timed window signal. One embodiment allows the prescribed threshold level and duration of the timed window signal to be programmably selected.

21 Claims, 4 Drawing Sheets

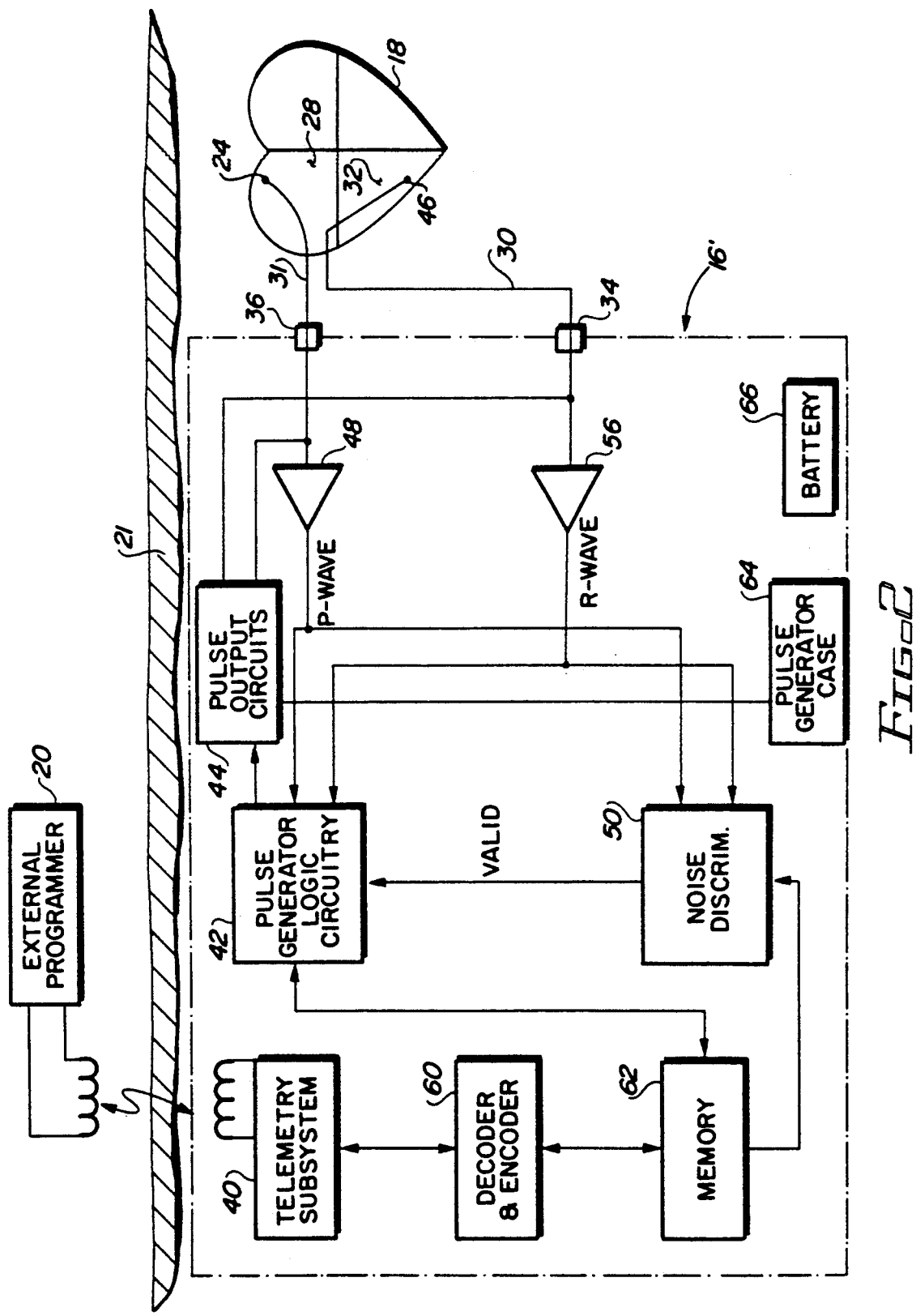

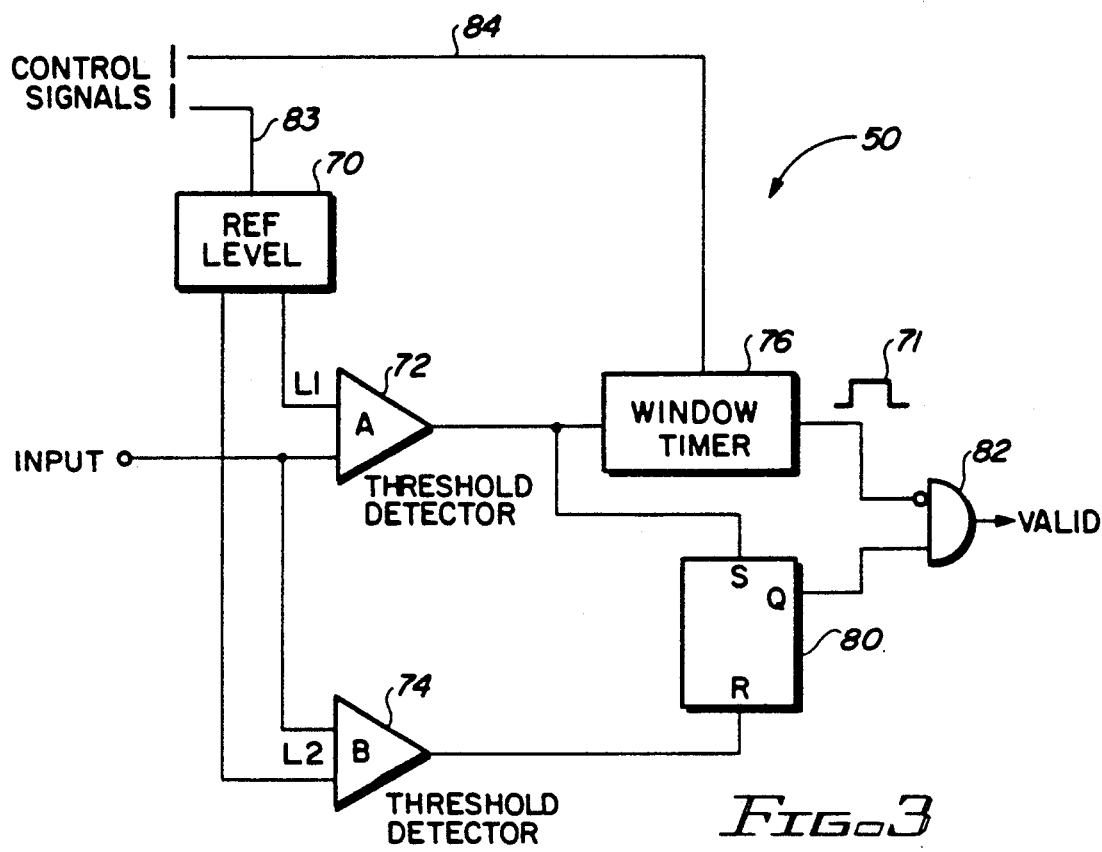
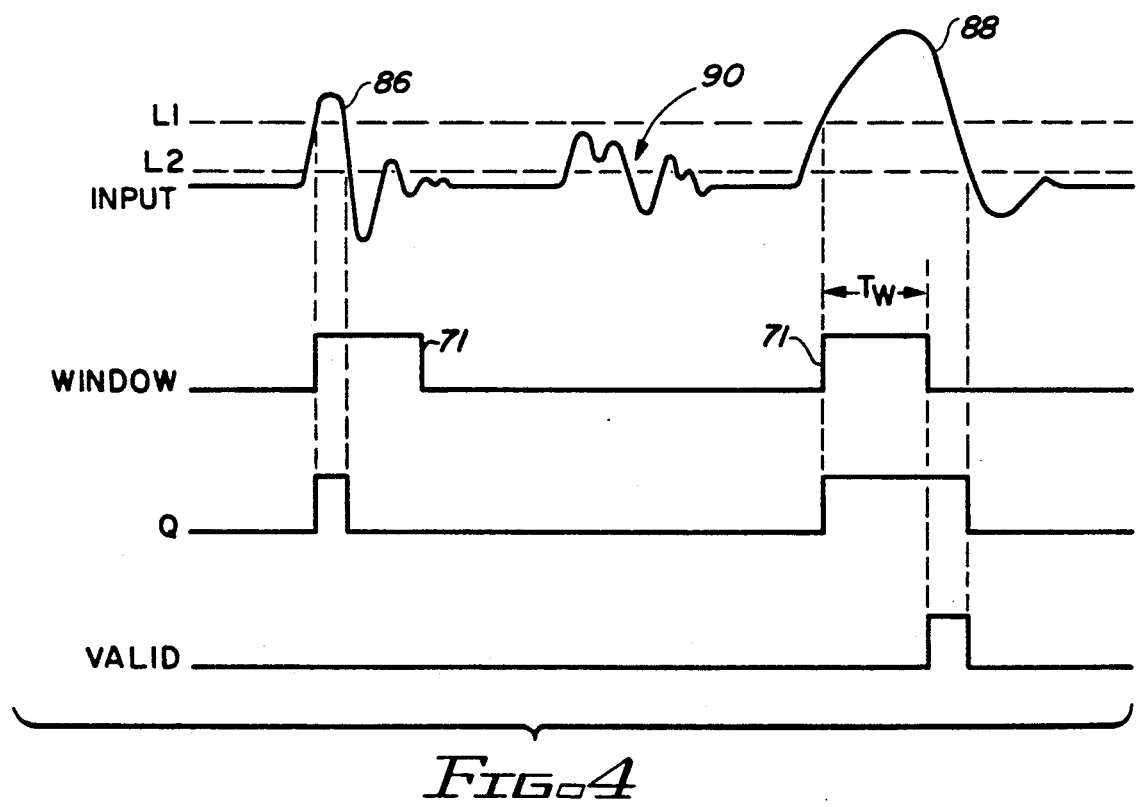

NOISE DISCRIMINATION IN IMPLANTABLE PACEMAKERS

BACKGROUND OF THE INVENTION

The present invention relates to apparatus and methods for discriminating noise from valid signals in implantable medical devices, such as implantable pacemakers or defibrillators.

A pacemaker is a medical device that assists the heart in maintaining a desired rhythm. The heart is a pump that circulates life-sustaining blood throughout the body. There are four chambers in a human heart, right and left atria, and right and left ventricles. Blood returning from the body enters the right atrium. When full, the right atrium contracts and forces the blood through the tricuspid valve into the right ventricle. Once the blood has passed into the right ventricle, the right ventricle contracts and pushes the blood into the lungs. After passing through the lungs, where wastes are expelled and new oxygen is received, the blood returns to the left atrium. When full, the left atrium contracts and forces the blood through the bicuspid valve into the left ventricle. From the left ventricle, the ventricle contracts and forces the blood throughout the body.

The right and left atria contract simultaneously, as do the right and left ventricle. There is a delay (typically of from 50-200 milliseconds for most adult human hearts) between the time the atria contract and the ventricles contract. This delay allows sufficient time for the blood to move from the atria into the ventricles. For the atria to contract, the atrial muscle tissue must first depolarize. When depolarization of the muscle tissue occurs, there is manifest an electrical signal known as a P-wave that can be detected using electrocardiographic (ECG) devices. (For most purposes, depolarization of cardiac tissue can be considered to occur concurrent with the contraction of cardiac tissue.) Similarly, for the ventricles to contract, the ventricular muscle tissue must first depolarize, causing an electrical signal known as an R-wave (or sometimes a QRS complex) to be manifest, which R-wave can also be detected. The R-wave is much larger than the P-wave because the muscle tissue surrounding the ventricles is more massive than the muscle tissue surrounding the atria (as the ventricles have to pump the blood much farther than do the atria). Typically, the rate at which the heart beats is measured from R-wave to R-wave, as the R-wave, i.e., contraction of the ventricular tissue, is the easiest event to detect. If the heart is beating at 60 beats per minute, for example, there is one beat per second, or 1000 milliseconds between ventricular contractions.

A pacemaker provides electrical stimulation pulses to either the right atrium and/or right ventricle in order to stimulate the muscle tissue to cause a contraction. Demand pacemakers monitor the heart, through the same electrical leads through which the stimulation pulses are provided, in order to sense the occurrence of a P-wave and/or R-wave ("P/R wave"). If a P/R wave is sensed, then there is no need to deliver a stimulation pulse. In such an instance (when a P/R wave is sensed), the delivery of the stimulation pulse in a demand pacemaker is inhibited, thereby conserving the limited power of the pacemaker's battery, and further preventing irregular rhythms (contractions) of the heart muscle tissue that might otherwise result. Thus, a demand pacemaker provides stimulation pulses to the right atrium and/or right ventricle on demand, i.e., only when needed.

Similarly, automatic defibrillators provide a high energy stimulation pulse to cardiac tissue in an attempt to start contractions in a heart that has stopped. If the heart responds to such high energy defibrillation pulses and starts beating on its own, as manifest by, e.g., the pressure of R-waves at a more or less constant rhythm, the need for defibrillation pulses ceases. Thus, an automatic defibrillator also operates in a demand mode, providing defibrillation pulses only when needed.

The ability of a demand pacemaker or automatic defibrillator to properly perform its function of providing stimulation pulses on demand is critically dependent upon its ability to detect P/R waves. Unfortunately, many electrical signals may be present in a typical ECG signal (that signal sensed through the pacemaker or defibrillator leads) that do not represent valid P/R waves. Such signals are referred to as noise, and the pacemaker or defibrillator sensing circuits must utilize some means of reliably differentiating between noise and valid P/R waves.

One common technique that can be used to reduce noise in a pacemaker, or other implantable medical device, is a filter that limits the frequency of the signals that are allowed to pass through it. Because noise signals, especially white noise, tend to occur randomly over the entire frequency spectrum, the use of a filter thus significantly reduces the amount of noise present. However, as the P/R waves are themselves pulses, representing specific cardiac events (i.e., the depolarization of the atrial and/or ventricular muscle tissue), the frequency bandwidth of any filters that are used with P/R detection circuits must be quite broad. See, e.g., U.S. Pat. No. 4,686,988. Further, much of the noise present in an intracardiac ECG signal is not white noise, but is noise lying in the same frequency range as the P/R waves. Further, as "noise" can be any unwanted electrical signal, even signals associated with the heart (such as a T wave), it is not possible to limit noise to specific frequency ranges. Hence, while filtering aids the discrimination process to a certain extent, it is not effective at removing all noise from the signal.

Another common technique used to better discriminate noise from valid P/R waves is to employ a threshold detector or level detector. Such a circuit only passes signals therethrough having an amplitude that exceeds a prescribed threshold (reference) level. With such a circuit, low amplitude noise signals are rejected. Unfortunately, many noise signals within an intracardiac ECG signal are of a higher amplitude than is the P wave, as the P wave itself is a relatively low amplitude signal. Further, in some instances, short noise spikes may be present that approach or even exceed the amplitude of the R-wave. Thus, merely using a level detector does not remove all the noise signals from the ECG signal.

In response to the shortcomings of the filter and threshold detector for reliably discriminating valid P/R waves from noise, many prior art devices teach differentiating the intracardiac or other ECG signal. This is done because the P/R waves, particularly the R-wave, have a characteristic slope associated therewith that, if detected, can help identify a valid P/R wave from noise. U.S. Pat. No. 4,000,461, for example, teaches amplifying, filtering and differentiating the R-wave signal. The differentiated R-wave signal provides a signal proportional to the slope of the R-wave. This differentiated signal is then rectified, to look at both positive and negative slopes, and applied to a threshold detector, so that only signals having a slope above a set threshold level are acted upon. Finally, the signal is applied to a time discriminator to determine if the minimum slope is maintained for a prescribed period of time.

Similarly, in EPO 0 104 452 A1, valid R-waves are distinguished from noise by differentiating the ECG signal, and passing the resulting differentiated signal through a processing scheme that includes threshold detectors, rectifiers, and time discriminators.

While differentiating the ECG signal provides some basis for detecting a valid R-wave, it is difficult to use differentiation for successfully detecting a valid P-wave. This is because the P-wave, unlike the R-wave, is a relatively small signal that does not necessarily possess a sharp or characteristic slope. Further, the circuitry needed to perform the differentiation and other processing (e.g., rectification and time discrimination), represents additional circuitry that must be powered and housed within the limited power and space requirements of an implantable pacemaker or other implantable medical device. What is needed, therefore, is a noise discrimination technique that can readily distinguish both P-waves and/or R-waves from noise, and do so without requiring a large number of additional circuit components that may adversely impact the limited space and power requirements of an implantable pulse generator.

The present invention advantageously addresses the above-identified needs by providing a simple, yet effective, discrimination circuit that monitors the ECG signal directly, without differentiation or equivalent slope detection means, to determine whether a given ECG signal pulse is a valid ECG signal, i.e., a valid P-wave or R-wave, or noise.

SUMMARY OF THE INVENTION

Noise discrimination is provided in accordance with the teachings of the present invention by monitoring the ECG signal to determine both the amplitude and duration of any signal pulses appearing thereon. The ECG signal thus monitored could be used by an implantable pacemaker, defibrillator, or other medical device that relies upon the accurate detection of P/R waves, or other signals or waveforms, in order to properly perform its function. Simply stated, if the amplitude of a given ECG signal pulse exceeds a prescribed threshold level for a prescribed time period, the pulse is considered to be a valid ECG signal, i.e., a valid P-wave or R-wave ("P/R wave"). The prescribed time period, or window, is preferably programmable, and may be selectably adjusted between maximum and minimum values.

To this basic noise discrimination approach, which rejects low level signals or narrow signals (spikes), additional timing constraints may be added in other embodiments to also reject high level signals that last too long. Thus, in such an embodiment, a low level pulse (of any duration), a short high level pulse, or a long high level pulse, would all be rejected as noise. Only a high level pulse having a duration that falls within a prescribed time window passes as a valid signal. Such embodiment allows the invention to not only detect valid P/R waves, as might be used, e.g., in an implantable pacemaker, but also to detect and/or discriminate different types of waveforms that indicate danger or other events as used by a defibrillator or a pacemaker programmed to detect and break tachycardias (rapid rhythms) of the heart.

In keeping with one aspect of this invention, noise discrimination is accomplished by initiating a time window having a prescribed duration of slightly less than the duration of an anticipated P/R wave whenever atrial/ventricular activity is sensed that exceeds a certain threshold level. If the sensed activity drops below a second threshold level (typically zero) during this time window, the activity is rejected as noise. If the sensed activity remains above this second threshold level through the entire time window, the activity is accepted as a valid P/R wave.

In one embodiment, a noise discrimination circuit in accordance with the present invention includes: a threshold detector for determining if the amplitude of the ECG signal exceeds a prescribed threshold level; a timer circuit for generating a timed window signal, triggered by the threshold detector whenever the ECG signal amplitude exceeds the prescribed threshold level; and logic circuitry for determining if the amplitude of the ECG signal remains above the threshold level for the duration of the timed window signal.

Advantageously, a further embodiment allows the prescribed threshold level and duration of the timed window signal to be programmably selected, thereby allowing the noise discrimination effects of the invention to be tailored to suit the needs of a particular patient.

A still further embodiment times how long the ECG pulse signal remains above the threshold level and rejects the pulse as noise if the time exceeds a preset (and programmable) maximum time.

It is thus one aspect of the invention to provide a noise discrimination circuit that may be used in an implantable medical device, where the implantable medical device includes sensing means for sensing electrical signals originating within human tissue with which the medical device is in electrical contact. Such noise discrimination circuit includes: (1) means for determining if an electrical signal sensed by the sensing means exceeds a prescribed threshold level; and (2) means for determining if the sensed electrical signal remains above the prescribed threshold level for at least a prescribed time period. The sensed electrical signal is considered as a valid signal only if it exceeds the prescribed threshold level for the first prescribed time period.

Another aspect of the invention adds a second prescribed time period, longer than the first prescribed time period, and further rejects the sensed electrical signal as noise if it remains above a prescribed amplitude threshold for a time period greater than the second prescribed time period. Thus, in accordance with this aspect of the invention, the sensed electrical signal is considered as a valid signal only if it exceeds the prescribed threshold level for the first prescribed time period but not for the second prescribed time period.

In accordance with another aspect of the invention, apparatus is provided for discriminating a valid electrocardiograph (ECG) signal from noise. This apparatus comprises: (1) first threshold means for sensing when the amplitude of the ECG signal exceeds a first threshold value; (2) second threshold means for sensing when the amplitude of the ECG signal is less than a second threshold value; (3) timer means for generating a window signal having a selected duration, the window signal being triggered whenever the ECG signal amplitude exceeds the first threshold level; (4) logic means coupled to the first threshold means, second threshold means, and timer means for generating a valid ECG signal pulse only if the amplitude of the ECG signal initially exceeds the first threshold value, thereby triggering the window signal, without thereafter becoming less than the second threshold value for the duration of the triggered window signal.

In keeping with yet a further aspect of the invention, there is provided a method of automatically discriminating a valid electrocardiographic (ECG) signal sensed by an implanted pacemaker from noise. Such method includes the steps of: (a) determining if the ECG signal sensed by the implantable pacemaker exceeds a prescribed threshold level; and (b) if so, determining if the sensed ECG signal remains above the prescribed threshold level for a prescribed time period that is at least a first time but not longer than a second time; and (c) if so, signaling a valid ECG signal.

It is a feature of the present invention to provide a simple noise discrimination circuit that consumes little power, occupies only a small space, and that can thus be advantageously incorporated into the tight packaging and low power requirements of modern day implantable pacemakers.

It is a further feature of the invention to provide such a noise discrimination circuit that performs its noise discrimination function in real time, without the need of differentiating, integrating or storing any signals.

BRIEF DESCRIPTION OF THE DRAWINGS

The above and other aspects, features and advantages of the present invention will be more apparent from the following more particular description thereof, presented in conjunction with the following drawings wherein:

FIG. 2 is a block diagram of a pacemaker that includes the noise discrimination circuit of the present invention;

FIG. 3 is a functional logic/schematic diagram of the noise discrimination circuit of FIG. 2;

FIG. 4 is a timing diagram illustrating the operation of the noise discrimination circuit of FIG. 3;

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

The present invention describes a noise discrimination circuit that is designed for use with an implantable or other medical device. The following description of the invention assumes the implantable medical device is a pacemaker, and that the invention is used to discriminate valid P/R waves from noise. However, it is to be understood that the invention is not so limited. Other kinds of medical devices could make use of the invention, such as automatic defibrillators; and the invention could be used for other functions than identifying valid P/R waves, such as detecting and/or discriminating ECG waveforms evidencing a dangerous condition, such as tachycardia.

Figure 1:
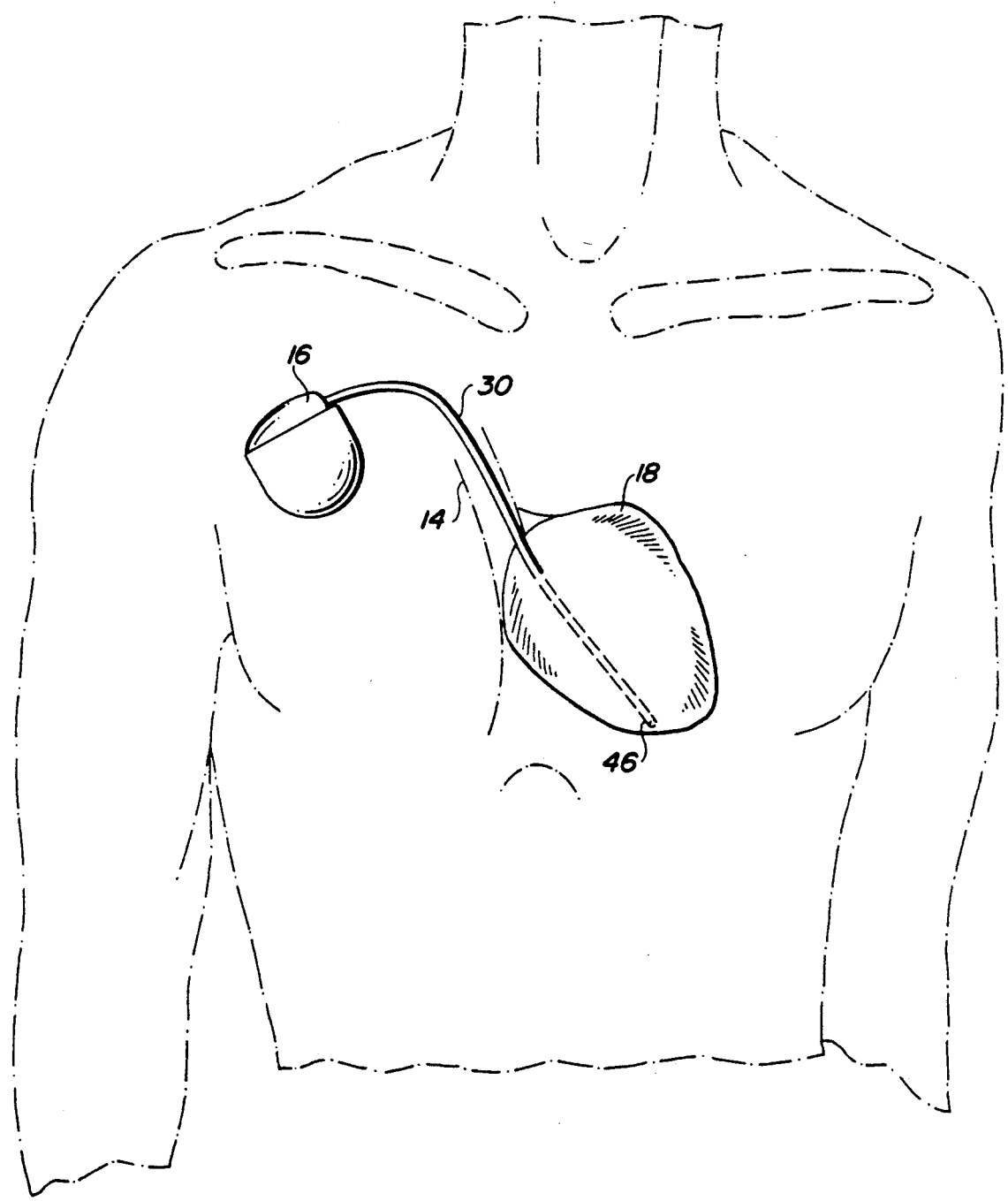
FIG. 1 shows an implantable pacemaker implanted in a patient.

With reference first to FIG. 1, and as an aid in understanding the manner in which a pacemaker is used, there is shown a pictorial diagram illustrating a pacemaker 16 that has been implanted in a patient 12. The pacemaker 16 is implanted in a suitable pocket made in the flesh of the patient, usually in the fleshy portions of the chest near the shoulder. A pacemaker lead 30 is then inserted intravenously through the superior vena cava 14, so that a distal end of the lead 30 finds its way into the heart 18. In FIG. 1, the lead 30 is inserted into the right ventricle of the heart, with a distal electrode 46 of the lead 30 being in contact with the inside wall of the right ventricle. Other configurations allow a lead to be placed in the right atrium in addition to, or in lieu of, the lead in the ventricle. The techniques used to implant a pacemaker are well known in the art.

As previously described in the Background portion of this application, it is the function of the pacemaker 16 to assist the heart 18 to maintain a regular rhythm of contractions, and thereby maintain an adequate flow of blood through the body. To this end, the pacemaker provides stimulation pulses to the heart only when the heart does not contract on its own within prescribed time limits. Thus, for instance, if 1200 milliseconds (or other set time period) after a first R-wave has been sensed, a second R-wave has not been sensed, the pacemaker circuits automatically deliver a stimulation pulse to the ventricle in an attempt to stimulate a ventricular contraction. A much more complete description of the manner in which modern implantable pacemakers function, including the various cardiac signals and sequences that are generated by the heart, and the various modes of operation in which the pacemaker may operate, may be found, e.g., in applicant's prior patent, U.S. Pat. No. 4,712,555, which patent is incorporated herein by reference.

Referring next to FIG. 2, a block diagram of a typical dual chamber pacemaker 16' is shown, including the noise discrimination circuit of the present invention. (A dual chamber pacemaker is one that interfaces with both the right atrium and the right ventricle. In contrast, a single chamber pacemaker, such as is shown in FIG. 1, paces and senses in only one chamber of the heart, such as the right ventricle. The noise discrimination circuit of the present invention may be utilized with either a single or dual chamber pacemaker.) The pacemaker 16' is in electrical contact with the patient's heart 18 by way of pacemaker leads 30 and 31, which leads are directed to the right ventricle 32 and right atrium 28, respectively. The atrial lead 31 includes a tip electrode 24 at its distal end that is in electrical contact with atrial tissue. Similarly, the ventricular lead 30 includes a tip electrode 46 at its distal end that is in electrical contact with ventricular tissue. Both the atrial lead 31 and the ventricular lead 30 are unipolar leads are in FIG. 2 as unipolar leads. In unipolar operation, the tip electrode 24 or 46 provides one signal path, with the return path being provided through conductive body fluids and tissue to an exposed portion of the pulse generator case 64. It is to be understood, however, that either one or both leads could be bipolar leads, having two electrodes, in which case the return path is provided through the other electrode (which other electrode is typically a ring electrode that is positioned only a few centimeters from the tip electrode).

The pacemaker is also in electromagnetic contact with an external programmer 20. The programmer 20 includes a telemetry receiver and monitor external to the patient's skin 21. The pacemaker 16' includes a telemetry subsystem 40 for transmitting data and parameter values to the external telemetry transmitter and receiver of the external programmer 20, and for receiving data instructions and the like from the external programmer 20. Data instructions received from the external programmer 20 are decoded in decoder and encoder 60 and stored in memory 62. Likewise, data and parameter values to be sent to the external programmer 20 are encoded in the decoder and encoder circuit 60 prior to transmission. The manner of establishing and operating a telemetry link between an external programmer and implantable medical device is known in the art.

The data instructions stored in the memory 62 control the operation of the pacemaker. In particular, the stimulation pulses generated by the pacemaker are generated in pulse output circuits 44 as triggered by appropriate trigger signals obtained from pulse generator logic circuitry 42. For example, if the pulse generator logic circuitry 42 determines that a stimulation pulse is required on the atrial channel, an atrial trigger signal is generated and presented to the pulse output circuits 44. In response to this trigger signal, a stimulation pulse is generated that is directed to the atrial tip electrode 24 through the atrial lead 31. In a similar manner, a ventricular stimulation pulse is generated as directed by the pulse generator logic circuitry 42 and presented to the ventricular electrode 46 over the ventricular lead 30.

When operating in a demand mode, stimulation pulses are provided as above described only in the absence of natural cardiac activity, i.e., only when the heart 18 is not beating (contracting) on its own. Natural cardiac activity is determined by monitoring the leads 30 and/or 31 for electrical activity indicative of muscle contraction. As indicated, atrial depolarization (and hence contraction) is manifest by the presence of a P-wave. Ventricular depolarization (and hence contraction) is manifest by the presence of an R-wave. Amplifier 48 senses the electrical signals appearing on the atrial lead or channel 31. Similarly, amplifier 56 senses the electrical signals appearing on the ventricular lead or channel 30. The signals present within both the atrial and ventricular channels are referred to herein as the intracardiac ECG signals. Typically, because amplifiers 48 and 56 have a limited bandwidth associated therewith, some preliminary filtering of the ECG signals takes place in these amplifiers.

The present invention includes a noise discrimination circuit 50 that monitors the ECG signals sensed on the ventricular and/or atrial channels 30 and 31, or through other available channels, as appearing at the output of amplifiers 56 and 48, to determine whether such signals are valid P/R waves or noise. If valid P/R waves, then a "valid" signal is sent to the pulse generator logic circuitry 42, allowing this pulse generator logic circuitry to inhibit the delivery of a stimulation pulse to the heart. If noise, i.e., if the "valid" signal is not generated, then the detected intracardiac ECG signal is rejected as noise, and a stimulation pulse may be delivered to the heart. It is thus critically important for the proper operation of the pacemaker 16' that the noise discrimination circuitry 50 of the present invention be able to accurately distinguish valid P/R waves from noise.

Referring next to FIG. 3, a functional logic/block diagram of a preferred noise discrimination circuit 50 is illustrated. It is to be noted that if a dual chamber pacemaker is employed, such as is shown in FIG. 2, two separate noise discrimination circuits of the type shown in FIG. 3 will typically be employed, one to discriminate P-waves from noise, and the other to discriminate R-waves from noise. However, as the operation of the noise discrimination circuit is essentially the same for both atrial and ventricular channels, only the circuit and its operation for one channel (atrial) will be described. (It is noted that the only substantive difference between an atrial noise discrimination circuit and a ventricular noise discrimination circuit in accordance with the present invention relates to the setting of the threshold levels and length of the time window generated by the window timer circuit as explained below.)

As seen in FIG. 3, the noise discrimination circuit 50 includes two threshold detectors 72 and 74, each of which has one of its two inputs connected to the input signal, i.e., the output of amplifier 48 (or amplifier 56). The other input of amplifier 72 is connected to a first threshold reference level signal L1. The other input of amplifier 74 is connected to a second threshold reference level signal L2. Both reference signals L1 and L2 are generated in a reference level signal generator circuit 70, which circuit 70 receives a control signal(s) from the pacemaker memory 62 (FIG. 2) over signal line(s) 83 specifying the particular reference level signals that are to be generated.

The output of threshold detector 72 is directed to a window a window timer circuit 72. Whenever the output of threshold detector 72 indicates that the amplitude of the input signal exceeds the reference level L1, the window timer 76 is triggered, thereby generating an output window pulse signal 71. The width of the window pulse signal 7i is controlled by a control signal received over signal line 84, which control signal is obtained from the pacemaker memory 62.

The output of threshold detector 72 is also directed to the set terminal of a latch circuit 80. Thus, whenever the window timer 76 is triggered, as occurs whenever the amplitude of the input signal exceeds the level L1, the latch circuit 80 is set. The output of threshold detector 74 is connected to the reset terminal of the latch circuit 80. Whenever the output signal of threshold detector 74 indicates that the amplitude of the input signal is less than reference level L2, the latch circuit 80 is reset.

The inverse of the window pulse signal 71 and the output of the latch circuit 80, labeled Q, are logically ANDED in gate 82. Thus, only when the latch circuit 80 remains set at the conclusion of the window pulse signal 71 does a pulse appear on the output of gate 82. This pulse is the "valid" signal indicating that a valid P/R wave has been detected.

The operation of the noise discrimination circuit 50 may be better understood with reference to the waveform timing diagram of FIG. 4. In FIG. 4, the input signal is illustrated as having a first noise spike 86, a second noise burst 90, and a valid P-wave pulse 88. Both the noise spike 86 and the P-wave pulse 88 exceed the threshold level L1. Hence, the window pulse 71 is generated in both instances. Similarly, the latch circuit 80 is set by both the noise spike 86 and the P-wave 88. The setting of the latch circuit is indicated by the Q signal going high. As soon as the amplitude of the noise spike drops below the second threshold level L2, the latch circuit is reset, as indicated by the Q signal going low. At the conclusion of the first window pulse 71 (the one triggered by the narrow noise spike 86), the latch is reset, thus no "valid" signal is generated. At the conclusion of the second window pulse, however, i.e., the window pulse triggered by the P-wave, the latch circuit has not been reset because the amplitude of the P-wave has not yet dropped below the second threshold level L2, thereby causing a "valid" signal to be generated.

Thus, it is seen that while both events 86 and 88 on the input signal cause the window pulse to be triggered, only the valid P-wave 88 causes a "valid" output signal to be generated because only the P-wave 88 maintains its amplitude above the second threshold level after exceeding the first threshold level for a period of time greater than the duration of the window pulse. Further, as is also seen in FIG. 4, the amplitude of the noise burst 90 never exceeds the first threshold level L1, and hence the window pulse 71 is not generated, and the latch circuit 80 is never set, thereby disabling gate 82 and blocking the generation of the "valid" signal.

It is to be emphasized that the noise discrimination circuit described in FIGS. 3 and 4 is primarily functional in nature. Thus, numerous variations could be made thereto by those skilled in the art for the purpose of achieving the same results. For example, it may be desirable to employ another latch circuit at the output of gate 82 in order to latch the "valid" signal that is generated, as the "valid" signal could otherwise vary in width from a very narrow sliver of a pulse to a very long pulse, depending upon the amount of time after the duration of the window pulse 71 that the ECG signal exceeds threshold level L2.

As indicated in FIG. 4, the duration of the window pulse 71 is identified as $T_w$ seconds. Advantageously, the value of $T_w$ may be programmably controlled or set to a desired value through a control signal that is loaded into the pacemaker's memory 62 from the programmer 20 (see FIG. 2). Typically, $T_w$ will be set to a value that is only slightly less than the expected width of the P wave or R wave. Similarly, the value of the threshold levels L1 and L2 may also be programmably controlled. In the usual instance, L1 will be set to a value that is 0.6 to 0.8 of the average amplitude of the expected P wave or R wave. L2 may be set to a value near zero. In some embodiments, L2 may be ground potential, in which case threshold detector 74 will function as a zero crossing detector. With L2 equal to ground, the reference level circuit 70 need only generate the reference level L1, as the reference level L2 will remain fixed at ground.

The programmable reference level circuit 70 may be realized using any suitable commercially available digital to analog (D-to-A) converter. Such D-to-A converter advantageously interfaces directly with the digital signals stored in the pacemaker memory 62. Such stored signals may thus define a group of possible threshold values that can be selected. Alternatively, a simple reference level generator circuit 70 could be readily fashioned by those skilled in the art, e.g., by using a plurality of zener diodes that are switchably coupled to the L1 and L2 signal lines as controlled by the digital control signal. Other reference circuits could be used that provide a threshold value that is infinitely adjustable within a specified range of possible threshold values.

The window timer circuit 76 may likewise be fashioned from commercially available components, such as a CMOS one shot multivibrator. Digital timer circuits are also available and readily known in the art. CMOS digital timer circuits offer the advantage of being able to interface directly with the digital control signal on signal line 84, while consuming very little power.

The threshold detector circuits 72 and 74 may be realized using commercially available comparator circuits or by properly configured operational amplifiers. Latch circuit 80 may be a conventional flip flop circuit having set and reset terminals. Logic gate 82 may be realized using commonly available invertor and other gates (AND, NAND, or NOR). Advantageously, all of the circuit elements shown in FIG. 3 can be fashioned using CMOS or other low power consuming technology, available in compact integrated circuits. In fact, it is possible for the entire noise discrimination circuit 50, as well as the pulse generator logic circuity 42, to be fabricated on a single semiconductor chip.

Figure 5:
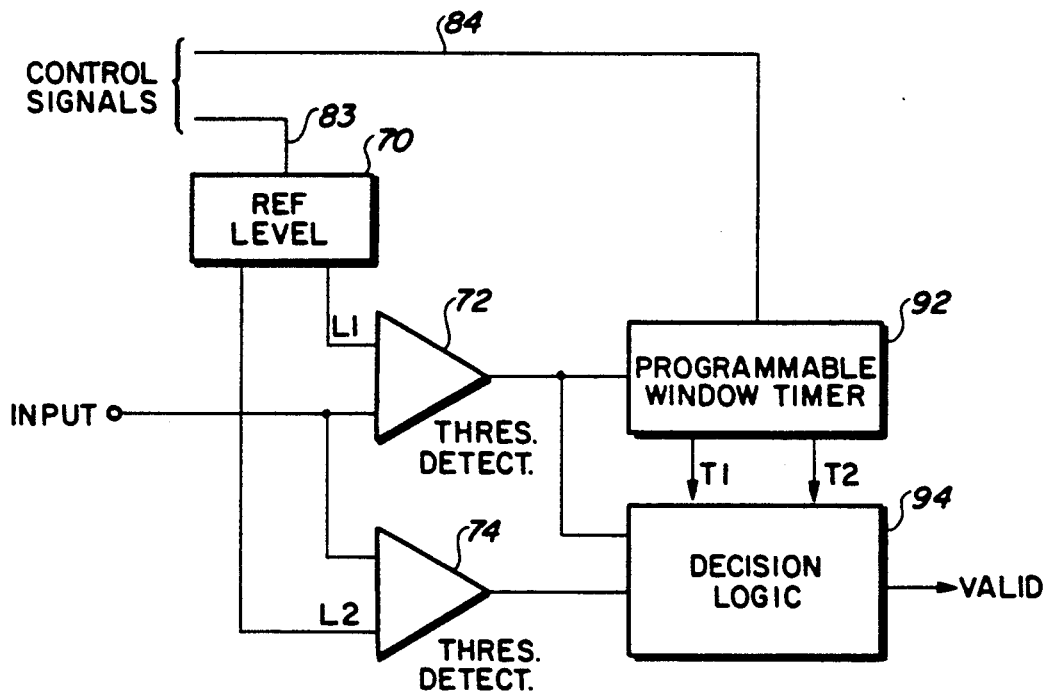
FIG. 5 is a block diagram of an alternative embodiment of the noise discrimination circuit of the present invention.
Figure 6:
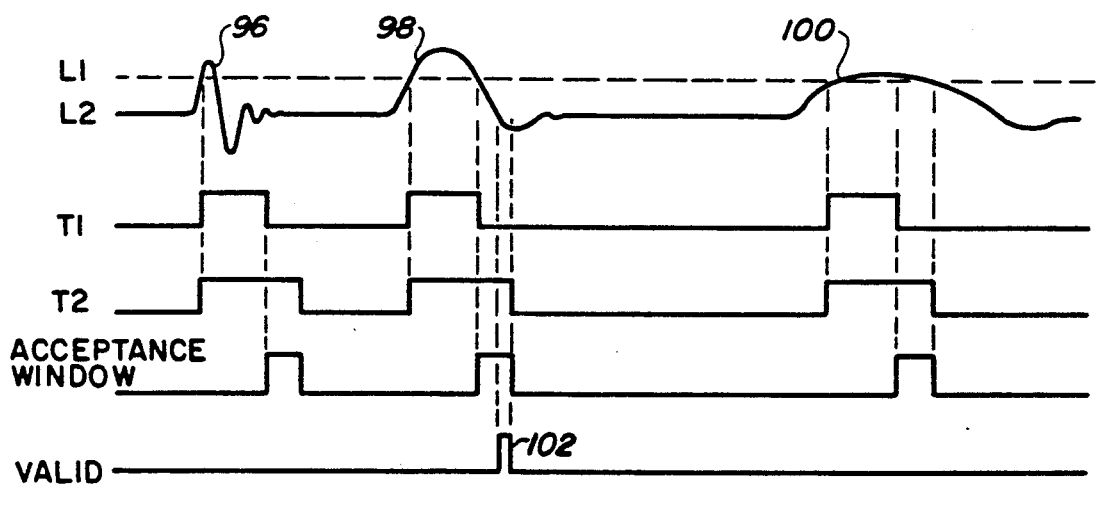
FIG. 6 is a timing diagram illustrating the operation of the noise discrimination circuit of FIG. 5.

Referring next to FIG. 5, a block diagram of an alternative embodiment of the present invention is illustrated. FIG. 6 depicts a timing diagram that illustrates the operation of the embodiment shown in FIG. 5. The following discussion refers to both figures jointly.

The noise discrimination circuit shown in FIG. 5 includes many of the same elements that are included in the noise discrimination circuit of FIG. 4. Those elements that may be the same as previously described in connection with FIG. 4 are identified by the same reference numerals as used in FIG. 4, and the description of these elements previously given in connection with FIG. 4 applies equally to the description given here. As seen, the input signal, which may be, e.g., an ECG signal, is applied to two threshold detectors 72 and 74. Programmable reference levels are applied to each threshold detector, a reference level L1 being applied to threshold detector 72, and a reference level L2 being applied to threshold detector 74. The reference levels are generated in the same manner as previously described. Further, the operation of the threshold detectors 72 and 74 is the same as previously described, i.e., threshold detector 72 changes its output level when the input signal exceeds reference level L1, and threshold detector 74 changes its output level when the input signal is less than reference level L2.

A programmable window timer circuit 92 is triggered by the output signal from the threshold detector 72. When triggered, i.e., as soon as the input signal exceeds the threshold level L1, the timer circuit 92 generates two programmable time periods, T1 and T2. Each time period begins at the trigger signal, but time T2 is longer than time T1, as shown in the timing diagram of FIG. 6. Decision logic 94 monitors the outputs from both threshold detector circuits 72 and 74, comparing these outputs with the time periods T1 and T2 for the purpose of determining whether the input signal drops below the threshold level L2 during a time period after T1 has expired, but prior to the expiration of T2. This time period, i.e., T2-T1, is defined as an Acceptance Window, and is depicted in the timing diagram of FIG. 6. The Acceptance Window thus begins a time T1 after the input signal exceeds threshold level L1, and lasts until the expiration of time T2.

In operation, if the input signal, after having initially increased above the threshold level L1, does not drop below the threshold level L2 until during the Acceptance Window, then the input signal is considered as a valid signal, and a valid pulse signal 102 is generated by the decision logic. If, on the other hand, the input signal drops below the threshold level L1 either before or after the Acceptance Window, then the input signal is rejected as noise and the valid pulse signal is not generated by the decision logic.

Thus, four responses are possible by the noise discrimination circuit in response to a signal on the input signal line. A first response, not shown in FIG. 6, is when the input signal does not exceed the threshold level L1. In such a case, the signal is rejected as noise because the threshold detector circuit 72 is not triggered, nor is the window timer circuit triggered. A second response occurs when a narrow noise spike 96, having an amplitude that exceeds the reference level L1, is received on the input signal line. In such a case, the window timer circuit is triggered, causing both time periods T1 and T2 to be generated, which action, in turn, causes the Acceptance Window to be defined within the decision logic 94. However, because the input signal has already dropped below the threshold L2 at a time prior to the Acceptance Window, the noise spike is rejected as noise.

A third response occurs when a P/R wave 98 appears on the input signal line. As with the second response described above, as soon as the amplitude of the P/R wave exceeds the threshold L1, the window timer is triggered and the Acceptance Window is defined. During the Acceptance Window, the P/R wave 98 drops below the threshold level L2, causing the decision logic to generate the valid pulse 102.

A fourth response occurs when a wide pulse 100, such as a T wave, appears on the input signal line. As with the second and third responses, as soon as the amplitude of this signal exceeds the threshold L1, the window timer is triggered and the Acceptance Window is defined. However, because the signal remains above the threshold L2 for the entire duration of the Acceptance Window, this signal is considered as noise, and the decision logic does not generate a valid pulse.

Thus, the embodiment of the noise discrimination circuit described in FIGS. 5 and 6 imposes both a minimum and maximum time period during which the input signal, having already exceeded a first threshold, must drop below a second threshold if the signal is to be considered as a valid signal. This embodiment is thus able to discriminate between noise signals that are too narrow as well as noise signals that are too wide.

It is noted that as shown in FIG. 6, the threshold level L2 is assumed to be approximately ground or zero volts. However, this is only exemplary, and other values of L2, as well as L1, T1, and T2 could be programmably selected using the control signals 83 and 84 as desired. Typically, the Acceptance Window will be defined (by programming appropriate values of T1 and T2) so that it is defined to begin at about 0.8 to 0.9 of the average expected P/R wave pulse width, and terminates at about 1.1 to 1.2 of the average expected P/R wave pulse width.

It is submitted that numerous types of circuits, from programmed microprocessors to discrete logic circuits, could readily be fashioned by those skilled in the art in order to realize the decision logic 94. A simple decision logic circuit, for example, may be similar to that shown in FIG. 4, but including an additional timer circuit to generate the time T2, and appropriate logic gates and latches to define the Acceptance Window. It is noted that while the Acceptance Window is described above as being defined as the difference between time periods T1 and T2, with both times T1 and T2 being initiated by the same trigger signal, it is also possible to define an acceptance time period that is triggered by the timing out of time period T1. Indeed, numerous variations of the manner in which the circuit may be fashioned are possible, all of which may readily perform the function of the noise discrimination circuit of the present invention.

As has been described above, it is thus seen that a simple noise discrimination circuit is provided that consumes little power, occupies only a small space, and that can be incorporated into the tight packaging and low power requirements of modern day implantable pacemakers. Moreover, such a circuit advantageously performs its noise discrimination function in real time, without the need of sampling and storing signals for later comparison, or without the need of differentiating or integrating the input signal.

The invention herein disclosed has been described by means of illustrative embodiments and applications that exemplify the currently considered preferred embodiments for such purposes. These descriptions have been provided by way of illustration and not limitation of the invention. Various modifications thereof will occur to those skilled in the art, and such modifications are within the scope of the claims that define the present invention.

What is claimed is:

1. A noise discrimination circuit used in an implantable medical device, said implantable medical device including sensing means for sensing electrical signals originating within heart tissue with which said medical device is in electrical contact, said sensing means comprising a single wire lead in contact with said heart tissue, said noise discrimination circuit comprising:

first and second threshold detectors coupled to the sensing means, the first threshold detector generating a first signal when the electrical signal sensed exceeds a first threshold value, the second threshold detector generating a second signal when the electrical signal sensed falls below a second threshold value;

timer means for generating a window signal having a prescribed time period, the window signal being triggered whenever the electrical signal sensed exceeds the first threshold value;

latch means for generating a latch signal upon the occurrence of the first signal and for terminating the latch signal upon the occurrence of the second signal; and means for designating the electrical signal sensed as being valid during an interval defined by the absence of the window signal and the presence of the latch signal.

2. The noise discrimination circuit as set forth in claim 1 wherein the electrical signals sensed includes a P-wave, wherein a valid P-wave comprises a cardiac electrical signal that exceeds said first threshold level for said prescribed time period, and wherein an invalid P-wave or noise comprises a cardiac electrical signal that does not exceed said first threshold level for said prescribed time period; whereby a valid P-wave is thereby discriminated from noise.

3. The noise discrimination circuit as set forth in claim 1 wherein the electrical signals sensed includes an R-wave, wherein a valid R-wave comprises a cardiac electrical signal that exceeds said prescribed threshold level for said prescribed time period, and wherein an invalid R-wave or noise comprises a cardiac electrical signal that does not exceed said first threshold level for said prescribed time period; whereby a valid R-wave is discriminated from noise.

4. The noise discrimination circuit as set forth in claim 3 further including programmable means for programmably adjusting the value of said first and second threshold values and the duration of said window signal.

5. Apparatus for discriminating a valid electrocardiograph (ECG) signal from noise comprising:
   first threshold means for sensing when the amplitude of said ECG signal exceeds a first threshold value;
   second threshold means for sensing when the amplitude of said ECG signal is less than a second threshold value;
   timer means for generating a window signal having a preselected duration, said window signal being triggered whenever said ECG signal amplitude exceeds said first threshold level; and
   logic means coupled to said first threshold means, second threshold means, and timer means for generating a valid ECG signal pulse only if the amplitude of said ECG signal initially exceeds said first threshold value, thereby triggering said window signal, without thereafter becoming less than said second threshold value for the duration of said window signal.

6. The discriminating apparatus as set forth in claim 5 wherein said first threshold mean comprises a threshold detector circuit including means for receiving said ECG signal and said first threshold value as input signals, and wherein said threshold detector circuit has an output signal that switches from one state to another state whenever the amplitude of said ECG signal exceeds said first threshold value.

7. The discriminating apparatus as set forth in claim 6 wherein said first threshold value is selectable from a group of possible threshold values.

8. The discriminating apparatus as set forth in claim 6 wherein said first threshold value is infinitely adjustable within a range of possible threshold values.

9. The discriminating apparatus as set forth in claim 5 wherein said second threshold means comprises a second threshold detector circuit including means for receiving said ECG signal and said second threshold value as input signals, and wherein said second threshold detector circuit has an output signal that switches from one state to another state whenever the amplitude of said ECG signal is less than said second threshold value.

10. The discriminating apparatus as set forth in claim 9 wherein said second threshold value is selectable from a range of possible threshold values.

11. The discriminating apparatus as set forth in claim 9 wherein said second threshold value is zero, whereby said second threshold detector circuit comprises a zero crossing detector circuit.

12. The discriminating apparatus as set forth in claim 5 wherein said logic means comprises:
   a latch circuit that is set whenever said ECG signal exceeds said first threshold level and is reset whenever said ECG signal is less than said second threshold level; and
   a logic gate that produces said valid ECG signal pulse only when said latch circuit remains set at the conclusion of said window signal.

13. The discriminating apparatus as set forth in claim 5 wherein said timer means comprises a timing circuit that generates said window signal as a window pulse having a leading edge and a trailing edge and a duration of $T_w$ seconds therebetween, the leading edge of said window pulse being coincident with the occurrence of said ECG signal exceeding said first threshold value, the trailing edge of said window pulse being coincident with the occurrence of said ECG falling below said second threshold value, thereby indicating the conclusion of said $T_w$ time period.

14. The discriminating apparatus as set forth in claim 13 wherein the time period $T_w$ is programmably selectable.

15. The discriminating apparatus as set forth in claim 5 wherein said timer means comprises a timing circuit that begins measuring a selectable time period $T_w$ upon the first occurrence of said ECG signal exceeding said first threshold level, and that generates a timed out signal at the conclusion of said time period $T_w$.

16. The discriminating apparatus as set forth in claim 15 wherein the time period $T_w$ is programmably selectable.

17. The discriminating apparatus as set forth in claim 15 further including means for defining a second time period that commences at the conclusion of said time period $T_w$, and further wherein said logic means includes means for generating said valid ECG signal pulse only if: (1) the amplitude of said ECG signal initially exceeds said first threshold value, thereby triggering said window signal, without thereafter becoming less than said second threshold value for the duration of said triggered window signal; and (2) the amplitude of said ECG signal becomes less than said second threshold value prior to the conclusion of said second time period.

18. The discriminating apparatus as set forth in claim 17 wherein the time period $T_w$ and said second time period are programmably selectable.

19. A method of automatically discriminating a valid electrocardiographic (ECG) signal sensed by an implanted pacemaker from noise comprising the steps of:
   (a) sensing an ECG signal;
   (b) determining if said ECG signal sensed by said implantable pacemaker exceeds a prescribed threshold level; and, if so,
   (c) determining if said sensed ECG signal remains above said prescribed threshold level for at least a prescribed time period; and, if so,
   (d) signaling a valid ECG signal.

20. The method set forth in claim 19 wherein the step of determining if said sensed ECG signal remains above said prescribed threshold level for at least said prescribed time period includes setting a latch circuit whenever said ECG signal exceeds said prescribed threshold level and resetting said latch circuit whenever said ECG signal is less than a second threshold level, said second threshold level being less than said prescribed threshold level; and determining if said latch circuit is set at the termination of said prescribed time period.

21. The method set forth in claim 19 wherein the step of determining if said sensed ECG signal remains above said prescribed threshold level for at least said prescribed time period includes determining if said ECG signal exceeds a second threshold level at the conclusion of said prescribed time period, said second threshold level being less than said prescribed threshold level.

* * * * *